US012629077B2

(12) United States Patent (10) Patent No.: US 12,629,077 B2
Meeker et al. (45) Date of Patent: May 19, 2026

(54) WEARABLE CARDIOVERTER DEFIBRILLATOR WITH IMPROVED ECG ELECTRODES

(71) Applicant: WEST AFFUM HOLDINGS DAC, Dublin (IE)

(72) Inventors: Dallas E. Meeker, Kirkland, WA (US); Kiah Lesher, Los Angeles, CA (US); Douglas K. Medema, Everett, WA (US); Robert R. Buchanan, Bothell, WA (US); Zoie R. Engman, Kirkland, WA (US); Phillip D. Foshee, Jr., Woodinville, WA (US); David P. Finch, Bothell, WA (US)

(73) Assignee: WEST AFFUM HOLDINGS DAC, Dublin (IE)

( * ) Notice: Subject to any disclaimer, the term of this patent is extended or adjusted under 35 U.S.C. 154(b) by 0 days.

(21) Appl. No.: 18/057,132

(22) Filed: Nov. 18, 2022

(65) Prior Publication Data

US 2023/0080668 A1 Mar. 16, 2023

Related U.S. Application Data

(63) Continuation of application No. 16/197,141, filed on Nov. 20, 2018, now Pat. No. 11,540,762, which is a
(Continued)

(51) Int. Cl.
A61B 5/282 (2021.01)
A61B 5/00 (2006.01)
(Continued)

(52) U.S. Cl.
CPC .............. A61B 5/282 (2021.01); A61B 5/361 (2021.01); A61B 5/4836 (2013.01); A61N 1/025 (2013.01);
(Continued)

(58) Field of Classification Search
CPC ..... A61B 5/282; A61B 5/6831; A61B 5/6843; A61B 5/361; A61B 5/4836; A61B 5/6805;
(Continued)

(56) References Cited

U.S. PATENT DOCUMENTS 3,724,355 A 4/1973 Busch et al.
3,724,455 A 4/1973 Unger
(Continued)

FOREIGN PATENT DOCUMENTS

CN 109157202 A 1/2019
DE 2005060985 A2 6/2007
(Continued)

OTHER PUBLICATIONS

Heartstart MRx and XL AED Algorithm-Application Note, Jul. 2001, Edition 2 Philips Healthcare, USA.
(Continued)

*Primary Examiner* — Mallika D Fairchild
(74) *Attorney, Agent, or Firm* — Seed Intellectual Property Law Group LLP

(57) ABSTRACT

A Wearable Cardioverter Defibrillator (WCD) system comprises an electrode assembly with a permeable ECG electrode and a moisture barrier. In some embodiments, the moisture barrier is configured to reduce drying out of the permeable ECG electrode to improve performance of the WCD system. In a further enhancement, some embodiments of the electrode assembly also include a pillow structure positioned on a non-skin-contacting surface of the electrode assembly to comfortably reduce movement artifact or noise in the received ECG signal.

20 Claims, 8 Drawing Sheets

High resistance patient contact material, Air creepage isolation

Low resistance patient contact material, Air creepage isolation

Related U.S. Application Data continuation-in-part of application No. 16/107,854, filed on Aug. 21, 2018, now Pat. No. 10,632,302, which is a continuation of application No. 15/800,027, filed on Oct. 31, 2017, now Pat. No. 10,080,886, which is a continuation of application No. 14/710,799, filed on May 13, 2015, now Pat. No. 9,833,607.

(60) Provisional application No. 62/748,987, filed on Oct. 22, 2018, provisional application No. 62/588,825, filed on Nov. 20, 2017, provisional application No. 62/072,818, filed on Oct. 30, 2014.

(51) Int. Cl.

| | |
|---|---|
| *A61B 5/0205* | (2006.01) |
| *A61B 5/024* | (2006.01) |
| *A61B 5/08* | (2006.01) |
| *A61B 5/11* | (2006.01) |
| *A61B 5/145* | (2006.01) |
| *A61B 5/1455* | (2006.01) |
| *A61B 5/324* | (2021.01) |
| *A61B 5/361* | (2021.01) |
| *A61B 5/363* | (2021.01) |
| *A61N 1/02* | (2006.01) |
| *A61N 1/39* | (2006.01) |

(52) U.S. Cl.
CPC ......... *A61N 1/3904* (2017.08); *A61N 1/3975* (2013.01); *A61N 1/3987* (2013.01); *A61B 5/0205* (2013.01); *A61B 5/024* (2013.01); *A61B 5/0816* (2013.01); *A61B 5/1112* (2013.01); *A61B 5/14542* (2013.01); *A61B 5/14551* (2013.01); *A61B 5/324* (2021.01); *A61B 5/363* (2021.01); *A61B 5/6805* (2013.01); *A61B 5/6831* (2013.01); *A61B 5/6843* (2013.01); *A61B 5/7225* (2013.01); *A61B 2562/0209* (2013.01); *A61B 2562/164* (2013.01); *A61B 2562/18* (2013.01)

(58) Field of Classification Search
CPC ...... A61B 2562/0209; A61B 2562/164; A61B 2562/18; A61N 1/025; A61N 1/3904; A61N 1/3975; A61N 1/3987
See application file for complete search history.

(56) References Cited

U.S. PATENT DOCUMENTS

| | | | |
|---|---|---|---|
| 4,422,461 A * | 12/1983 | Glumac | A61N 1/0492 607/152 |
| 4,580,339 A * | 4/1986 | Ioffe | H01R 43/00 600/397 |
| 4,583,524 A | 4/1986 | Hutchins | |
| 4,619,265 A | 10/1986 | Morgan et al. | |
| 4,666,432 A | 5/1987 | McNeish et al. | |
| 4,698,848 A | 10/1987 | Buckley | |
| 4,928,690 A | 5/1990 | Heilman et al. | |
| 4,938,231 A * | 7/1990 | Milijasevic | A61N 1/0587 607/129 |
| 4,955,381 A | 9/1990 | Way et al. | |
| 4,979,517 A * | 12/1990 | Grossman | A61N 1/046 607/153 |
| 5,078,134 A | 1/1992 | Heilman et al. | |
| 5,228,449 A | 7/1993 | Christ et al. | |
| 5,348,008 A | 9/1994 | Bornn et al. | |
| 5,353,793 A | 10/1994 | Bornn | |
| RE34,800 E | 11/1994 | Hutchins | |
| 5,394,892 A | 3/1995 | Kenny et al. | |
| 5,405,362 A | 4/1995 | Kramer et al. | |
| 5,429,593 A | 7/1995 | Matory | |
| 5,474,574 A | 12/1995 | Payne et al. | |
| 5,506,059 A * | 4/1996 | Robbins | G02B 5/0858 428/458 |
| 5,618,208 A | 4/1997 | Crouse et al. | |
| 5,662,690 A | 9/1997 | Cole et al. | |
| 5,708,978 A | 1/1998 | Johnsrud | |
| 5,741,306 A | 4/1998 | Glegyak et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,108,197 A | 8/2000 | Janik | |
| 6,125,298 A * | 9/2000 | Olson | A61N 1/3925 607/5 |
| 6,148,233 A | 11/2000 | Owen et al. | |
| 6,201,992 B1 | 3/2001 | Freeman | |
| 6,263,238 B1 | 7/2001 | Brewer et al. | |
| 6,280,461 B1 | 8/2001 | Glegyak et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,779 B1 * | 3/2002 | Katzenmaier | A61N 1/046 607/152 |
| 6,356,785 B1 | 3/2002 | Snyder et al. | |
| 6,427,083 B1 | 7/2002 | Owen et al. | |
| 6,437,083 B1 | 8/2002 | Brack et al. | |
| 6,450,942 B1 | 9/2002 | Lapanashvili et al. | |
| 6,529,875 B1 | 3/2003 | Nakajima et al. | |
| 6,546,285 B1 | 4/2003 | Owen et al. | |
| 6,671,545 B2 | 12/2003 | Fincke | |
| 6,681,003 B2 | 1/2004 | Linder et al. | |
| 6,687,523 B1 | 2/2004 | Jayaramen et al. | |
| 6,762,917 B1 | 7/2004 | Verbiest et al. | |
| 7,065,401 B2 | 6/2006 | Worden | |
| 7,559,902 B2 | 7/2009 | Ting et al. | |
| 7,753,759 B2 | 7/2010 | Pintor et al. | |
| 7,762,953 B2 | 7/2010 | Derchak et al. | |
| 7,816,628 B2 | 10/2010 | Fernandez et al. | |
| 7,865,238 B2 | 1/2011 | Brink | |
| 7,870,761 B2 | 1/2011 | Valentine et al. | |
| 7,974,689 B2 | 7/2011 | Volpe et al. | |
| 8,135,462 B2 | 3/2012 | Owen et al. | |
| 8,140,154 B2 | 3/2012 | Donnelly et al. | |
| 8,369,944 B2 | 2/2013 | Macho et al. | |
| 8,467,860 B2 | 6/2013 | Salazar et al. | |
| 8,527,028 B2 | 9/2013 | Kurzweil et al. | |
| 8,548,557 B2 | 10/2013 | Garstka et al. | |
| 8,560,044 B2 | 10/2013 | Kurzweil et al. | |
| 8,615,295 B2 | 12/2013 | Savage et al. | |
| 8,639,348 B2 | 1/2014 | Geheb | |
| 8,644,925 B2 | 2/2014 | Volpe et al. | |
| 8,676,313 B2 | 3/2014 | Volpe et al. | |
| 8,706,215 B2 | 4/2014 | Kaib et al. | |
| 8,706,255 B2 | 4/2014 | Phillips et al. | |
| 8,742,349 B2 | 6/2014 | Urbon et al. | |
| 8,880,196 B2 | 11/2014 | Kaid | |
| 8,897,860 B2 | 11/2014 | Volpe et al. | |
| 8,904,214 B2 | 12/2014 | Volpe et al. | |
| 8,925,392 B2 | 1/2015 | Esposito et al. | |
| 8,965,500 B2 | 2/2015 | Macho et al. | |
| 9,008,801 B2 | 4/2015 | Kaib et al. | |
| 9,014,824 B2 | 4/2015 | Kroll-Orywahl et al. | |
| 9,084,583 B2 | 7/2015 | Mazar et al. | |
| 9,089,685 B2 | 7/2015 | Sullivan et al. | |
| 9,119,547 B2 | 9/2015 | Cazares et al. | |
| 9,131,901 B2 | 9/2015 | Volpe et al. | |
| 9,132,267 B2 | 9/2015 | Kaib | |
| 9,174,061 B2 | 11/2015 | Freeman et al. | |
| 9,265,432 B2 | 2/2016 | Warren et al. | |
| 9,345,898 B2 | 5/2016 | Piha et al. | |
| 9,381,373 B2 | 7/2016 | Geheb et al. | |
| 9,408,548 B2 | 8/2016 | Volpe et al. | |
| 9,427,564 B2 | 8/2016 | Kaib et al. | |
| 9,445,719 B2 | 9/2016 | Libbus et al. | |
| 9,454,219 B2 | 9/2016 | Volpe et al. | |

(56) References Cited

U.S. PATENT DOCUMENTS

| | | | |
|---|---|---|---|
| 9,566,033 B2 | 2/2017 | Bogdanovich et al. | |
| 9,579,020 B2 | 2/2017 | Libbus et al. | |
| 9,592,403 B2 | 3/2017 | Sullivan | |
| 9,598,799 B2 | 3/2017 | Shoshani et al. | |
| 9,675,804 B2 | 6/2017 | Whiting et al. | |
| 9,808,196 B2 | 11/2017 | Macia Barber et al. | |
| 9,878,171 B2 | 1/2018 | Kaib | |
| 9,895,105 B2 | 2/2018 | Romem | |
| 9,901,741 B2 | 2/2018 | Chapman et al. | |
| RE46,926 E | 7/2018 | Bly et al. | |
| 10,016,613 B2 | 7/2018 | Kavounas | |
| 10,076,656 B2 | 9/2018 | Dar et al. | |
| 10,143,405 B2 | 12/2018 | Jayalath et al. | |
| 10,192,387 B2 | 1/2019 | Brinig et al. | |
| 10,307,133 B2 | 6/2019 | Kaib | |
| 10,463,867 B2 | 11/2019 | Kaib et al. | |
| 10,589,110 B2 | 3/2020 | Oskin et al. | |
| 10,599,814 B2 | 3/2020 | Landrum et al. | |
| 2002/0181680 A1 | 12/2002 | Linder et al. | |
| 2003/0158593 A1 | 8/2003 | Heilman et al. | |
| 2004/0249432 A1 | 12/2004 | Cohen | |
| 2005/0004509 A1 | 1/2005 | Sun et al. | |
| 2005/0054941 A1 | 3/2005 | Ting et al. | |
| 2005/0107833 A1 | 5/2005 | Freeman et al. | |
| 2005/0107834 A1 | 5/2005 | Freeman et al. | |
| 2005/0148996 A1 | 7/2005 | Sun et al. | |
| 2006/0117805 A1 | 6/2006 | Valentine et al. | |
| 2006/0155183 A1* | 7/2006 | Kroecker | A61B 5/1112 |
| | | | 600/509 |
| 2006/0173499 A1 | 8/2006 | Hampton et al. | |
| 2006/0178706 A1 | 8/2006 | Lisogurski et al. | |
| 2007/0299325 A1 | 12/2007 | Farrell et al. | |
| 2007/0299474 A1 | 12/2007 | Brink | |
| 2008/0136652 A1* | 6/2008 | Vaisnys | A61N 1/3904 |
| | | | 340/635 |
| 2008/0183082 A1 | 7/2008 | Farringdon et al. | |
| 2008/0312709 A1 | 12/2008 | Volpe et al. | |
| 2009/0005827 A1 | 1/2009 | Weintraub et al. | |
| 2010/0007413 A1 | 1/2010 | Herleikson | |
| 2010/0298899 A1 | 11/2010 | Donnelly et al. | |
| 2011/0022105 A9 | 1/2011 | Owen et al. | |
| 2011/0071611 A1* | 3/2011 | Khuon | A61N 1/0492 |
| | | | 607/142 |
| 2011/0098593 A1* | 4/2011 | Low | A61B 5/274 |
| | | | 600/544 |
| 2011/0275915 A1 | 11/2011 | Allgeyer | |
| 2011/0288604 A1* | 11/2011 | Kaib | A61N 1/3925 |
| | | | 607/149 |
| 2011/0288605 A1* | 11/2011 | Kaib | A61B 5/6823 |
| | | | 607/5 |
| 2012/0003862 A1* | 1/2012 | Newman | A61B 5/273 |
| | | | 439/488 |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0191476 A1 | 7/2012 | Reid et al. | |
| 2012/0265265 A1 | 10/2012 | Razavi et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0085538 A1 | 4/2013 | Volpe et al. | |
| 2013/0144355 A1 | 6/2013 | Macho et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0281795 A1 | 10/2013 | Varadan | |
| 2013/0317852 A1 | 11/2013 | Worrell et al. | |
| 2013/0325078 A1 | 12/2013 | Whiting et al. | |
| 2014/0012144 A1 | 1/2014 | Crone | |
| 2014/0025131 A1 | 1/2014 | Sullivan et al. | |
| 2014/0039595 A1 | 2/2014 | Kroll-Orywahl et al. | |
| 2014/0046391 A1 | 2/2014 | Cowan et al. | |
| 2014/0070957 A1 | 3/2014 | Longinotti-Buritonil et al. | |
| 2014/0163663 A1 | 6/2014 | Poddar et al. | |
| 2014/0206948 A1 | 7/2014 | Romem | |
| 2014/0206974 A1 | 7/2014 | Volpe et al. | |
| 2014/0209351 A1* | 7/2014 | Reinhardt | A61N 1/0452 |
| | | | 174/126.2 |
| 2014/0249613 A1 | 9/2014 | Kaib | |
| 2014/0275823 A1* | 9/2014 | Lane | A61B 5/28 |
| | | | 600/372 |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2015/0047091 A1* | 2/2015 | Fournier | A41D 1/005 |
| | | | 2/69 |
| 2015/0148858 A1 | 5/2015 | Kaib | |
| 2015/0161554 A1 | 6/2015 | Sweeney et al. | |
| 2015/0202429 A1 | 7/2015 | Fritzsche | |
| 2015/0283391 A1 | 10/2015 | Meeker | |
| 2015/0297135 A1 | 10/2015 | Shoshani et al. | |
| 2015/0321022 A1 | 11/2015 | Sullivan et al. | |
| 2015/0328472 A1 | 11/2015 | Sullivan et al. | |
| 2015/0370320 A1 | 12/2015 | Connor | |
| 2016/0004831 A1 | 1/2016 | Carlson et al. | |
| 2016/0076175 A1 | 3/2016 | Rock et al. | |
| 2016/0076176 A1 | 3/2016 | Rock et al. | |
| 2016/0082277 A1 | 3/2016 | Foshee, Jr. et al. | |
| 2016/0113581 A1 | 4/2016 | Amir et al. | |
| 2016/0121100 A1* | 5/2016 | Crone | A61N 1/0492 |
| | | | 607/142 |
| 2016/0256104 A1 | 9/2016 | Romem et al. | |
| 2016/0283900 A1 | 9/2016 | Johnson et al. | |
| 2017/0014073 A1 | 1/2017 | Shoshani et al. | |
| 2017/0027469 A1 | 2/2017 | Amir et al. | |
| 2017/0036066 A1 | 2/2017 | Chahine | |
| 2017/0040758 A1 | 2/2017 | Amir et al. | |
| 2017/0162840 A1 | 6/2017 | Pendry | |
| 2017/0319862 A1 | 11/2017 | Foshee, Jr. et al. | |
| 2017/0367591 A1 | 12/2017 | Jorgenseon | |
| 2018/0014780 A1 | 1/2018 | Sotzing et al. | |
| 2018/0055400 A1 | 3/2018 | Dodemont | |
| 2018/0116537 A1 | 5/2018 | Sullivan et al. | |
| 2018/0117299 A1 | 5/2018 | Gustavson et al. | |
| 2018/0184933 A1 | 7/2018 | Sullivan et al. | |
| 2018/0185662 A1 | 7/2018 | Foshee, Jr. et al. | |
| 2018/0243578 A1 | 8/2018 | Volosin | |
| 2018/0361165 A1 | 12/2018 | Jaax et al. | |
| 2019/0030352 A1 | 1/2019 | Sullivan et al. | |
| 2019/0076666 A1 | 3/2019 | Medema | |
| 2019/0116896 A1 | 4/2019 | Armour et al. | |
| 2019/0321650 A1 | 10/2019 | Raymond et al. | |

FOREIGN PATENT DOCUMENTS

| | | | |
|---|---|---|---|
| EP | 2305110 A1 | 4/2011 | |
| EP | 3251587 A1 | 6/2017 | |
| JP | 4320257 A | 3/2005 | |
| JP | 5176202 B2 | 5/2008 | |
| JP | 5963767 A | 1/2014 | |
| JP | 5965913 B2 | 1/2014 | |
| JP | 2014526282 A | 10/2014 | |
| JP | 6407881 B2 | 3/2016 | |
| KR | 201000063651 A | 6/2010 | |
| KR | 20130137327 A | 12/2013 | |
| KR | 20160140956 A | 4/2014 | |
| KR | 101494865 B1 | 2/2015 | |
| KR | 101536139 B1 | 3/2015 | |
| KR | 101641643 B1 | 3/2015 | |
| KR | 20160108588 A | 9/2016 | |
| KR | 101383806 B1 | 4/2017 | |
| KR | 20170136083 A | 12/2017 | |
| RU | 171819 U1 | 6/2017 | |
| TW | I274576 B | 4/2007 | |
| TW | 201023826 A | 7/2010 | |
| TW | 201316950 A | 5/2013 | |
| WO | 98/39061 A2 | 9/1998 | |
| WO | 1998039061 A2 | 9/1998 | |
| WO | 2006009830 A2 | 1/2006 | |
| WO | 2010151875 A1 | 12/2010 | |

(56) References Cited

FOREIGN PATENT DOCUMENTS

| | | | |
|---|---|---|---|
| WO | 2011/146448 | A1 | 11/2011 |
| WO | 2012064604 | A1 | 5/2012 |
| WO | 2012/151160 | A1 | 11/2012 |
| WO | 2012176193 | A1 | 12/2012 |
| WO | 2015/056262 | A1 | 4/2015 |
| WO | 2016061709 | A1 | 4/2016 |
| WO | 2018129718 | A1 | 7/2018 |

OTHER PUBLICATIONS

Klein, H. U., Goldenberg, I., and Moss, A. J., "Risk Stratification for Implantable Cardioverter Defibrillator Therapy: The Role of the Wearable Cardioverter-Defibrillator, Clinical update," European Heart Journal, May 31, 2013, pp. 1-14, doi:10.1093/eurheartj/eht167, European Society of Cardiology.
LifeVest Model 4000 Patient Manual, Zoll, 2009, PN 20B0047 Rev B.
Pagan-Carlo, et al., "Encircling Overlapping Multipulse Shock Waveforms for Transthoracic Defibrillation," JACC Journals, Dec. 1998, vol. 32 Issue 7, p. 2065-2071.
The LifeVest Network/Patient Data Management System, Zoll, 2015, 2000503 Rev A.
Zoll, LifeVest, Proven protection from Sudden Cardiac Death, issued Mar. 27, 2018, 4 pages. Pittsburgh PA, USA.
International Search Report and Written Opinion for PCT Application No. PCT/US2015/051726, dated May 20, 2016, European Patent Office, Rijswijk, 11 pages.
European Examination Report mailed Jun. 15, 2022, issued in corresponding European Application No. EP 22155469.4, filed Oct. 26, 2015, 8 pages.
EP Office Action dated Sep. 30, 2021, EP Application No. 15 191 436.3-1122; pp. 1-3.
European Search Report dated Mar. 14, 2016; issued in European Application No. EP 15191436.3; 7 pages.
Heartstart MRx and XL AED Algorithm—Application Note, Jul. 2001, Edition 2 Phillips Healthcare, USA.
JP Office Action dated Oct. 5, 2021; JP Application No. 2019-35091; pp. 1-8 (translation provided) for 16 pages total.
Klein, H. U., Goldenberg I., & Moss, A. J., Risk Stratification for Implantable Cardioverter Defibrillator Therapy: The Role of the Wearable Cardioverter-Defibrillator, Clinical update, European Heart Jounal, May 31, 2013, pp. 1-14, doi:10.1093/eurheartj/eht167, European Society of Cardiology.
Lifecor LifeVest System Model WCD 3100 Operator's Manual, 2006, PN 20B0040 Rev FI, Zoll Lifecor Corporation, Pittsburgh, PA.
Machine Translation of Published Korean Patent Document KR 101383806 B1; published Apr. 9, 2014 (as procured from web by service of KIPO); 16 pages total.
ZOLL LifeVest Model 4000 Patient Manual PN 20B0047 Rev B, (C) 2009-2012.

* cited by examiner

100
EXTERNAL
DEFIBRILLATOR

SAMPLE COMPONENTS OF EXTERNAL DEFIBRILLATOR

307

303

301

309

311

313

305

401    403

Skin

405

High resistance patient contact material, Air creepage isolation

Low resistance patient contact material, Air creepage isolation

High resistance 903

Patient skin 901

900

Low resistance conductor and wire 905

907 Insulating

High resistance patient contact material, insulated isolation

Low resistance 1009

1001 Patient skin

1000

High resistance 1003

Low resistance conductor and wire 1005

1007 Insulation

Low resistance patient contact material, insulated isolation

1100

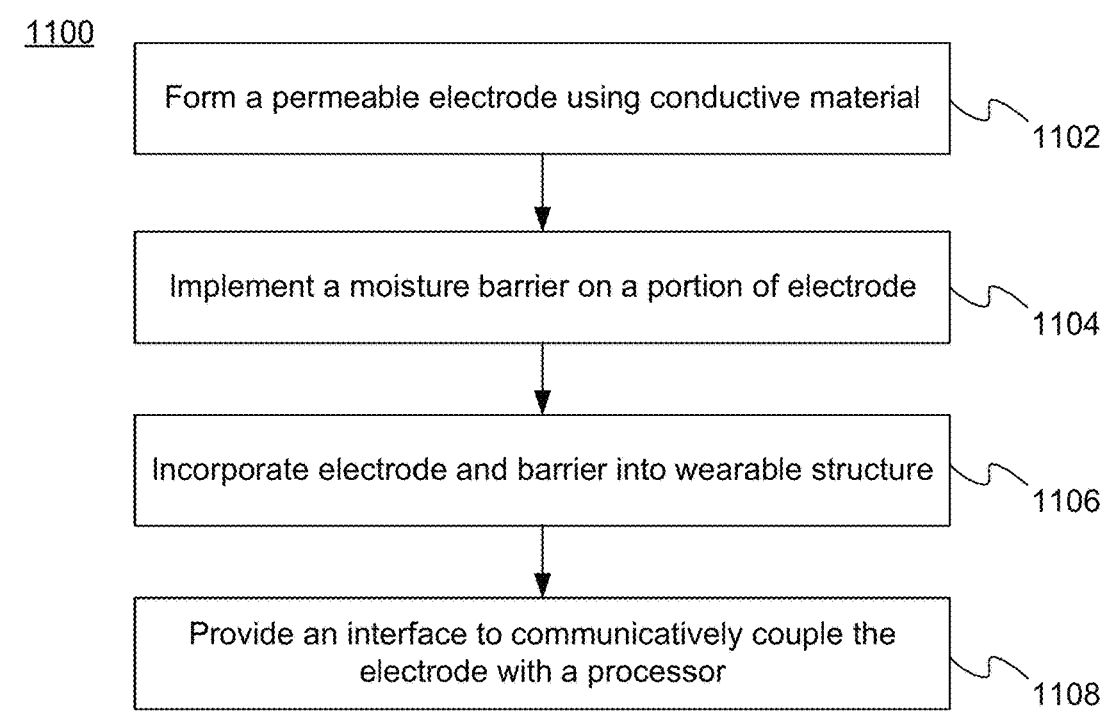

Form a permeable electrode using conductive material    1102

Implement a moisture barrier on a portion of electrode    1104

Incorporate electrode and barrier into wearable structure    1106

Provide an interface to communicatively couple the electrode with a processor    1108

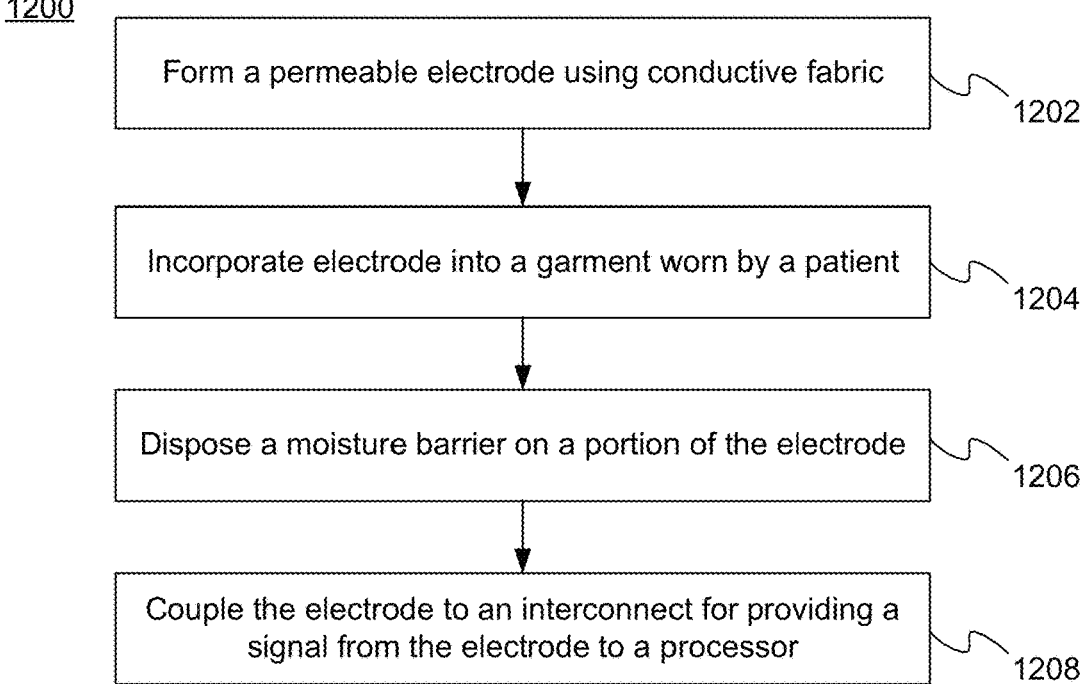

Form a permeable electrode using conductive fabric    1202

Incorporate electrode into a garment worn by a patient    1204

Dispose a moisture barrier on a portion of the electrode    1206

Couple the electrode to an interconnect for providing a signal from the electrode to a processor    1208

FIG. 12

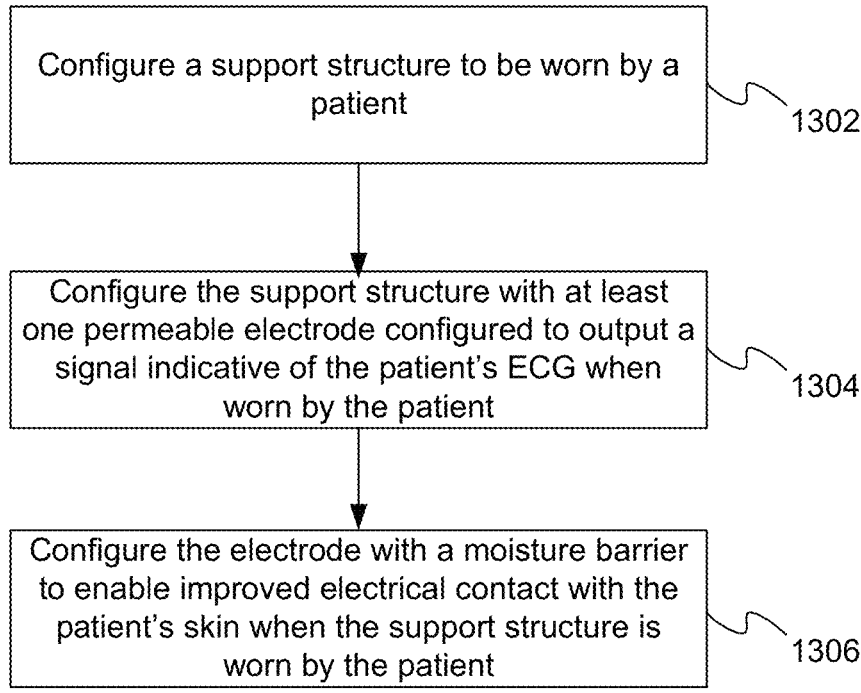

1300

Configure a support structure to be worn by a patient 1302

Configure the support structure with at least one permeable electrode configured to output a signal indicative of the patient's ECG when worn by the patient 1304

Configure the electrode with a moisture barrier to enable improved electrical contact with the patient's skin when the support structure is worn by the patient 1306

FIG. 13

WEARABLE CARDIOVERTER DEFIBRILLATOR WITH IMPROVED ECG ELECTRODES

CROSS REFERENCE TO RELATED PATENT APPLICATIONS

This patent application is a continuation of U.S. patent application Ser. No. 16/197,141, filed on Nov. 20, 2018, which claims priority from U.S. Provisional Patent Application No. 62/588,825, filed on Nov. 20, 2017, and U.S. Provisional Patent Application No. 62/748,987, filed on Oct. 22, 2018, and is a continuation-in-part of U.S. patent application Ser. No. 16/107,854, filed on Aug. 21, 2018, now U.S. Pat. No. 10,632,302, issued Apr. 8, 2020, which is a continuation of U.S. patent application Ser. No. 15/800,027, filed on Oct. 31, 2017, now U.S. Pat. No. 10,080,886, issued Sep. 25, 2018, which is a continuation of U.S. patent application Ser. No. 14/710,799, filed May 13, 2015, now U.S. Pat. No. 9,833,607, issued Dec. 5, 2017, which claims priority from U.S. Provisional Patent Application No. 62/072,818, filed on Oct. 30, 2014, the disclosures of which are hereby incorporated by reference.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g., within 10 minutes, unless treated in the interim. Some observers have thought that SCA is the same as a heart attack, which it is not.

Some people have an increased risk of SCA. Such people include patients who have had a heart attack, or a prior SCA episode. A frequent recommendation for these people is to receive an Implantable Cardioverter Defibrillator (ICD). The ICD is surgically implanted in the chest, and continuously monitors the patient's electrocardiogram (ECG). If certain types of heart arrhythmias are detected, then the ICD delivers an electric shock through the heart.

As a further precaution, people who have been identified to have an increased risk of an SCA are sometimes given a Wearable Cardioverter Defibrillator (WCD) system, to wear until the time that their ICD is implanted. Early versions of such systems were called wearable cardiac defibrillator systems. A WCD system typically includes a harness, vest, belt, or other garment that the patient is to wear. The WCD system further includes electronic components, such as a defibrillator and electrodes, coupled to the harness, vest, or other garment. When the patient wears the WCD system, the electrodes may make good electrical contact with the patient's skin, and therefore can help sense the patient's ECG. If a shockable heart arrhythmia is detected from the ECG, then the defibrillator delivers an appropriate electric shock through the patient's body, and thus through the heart. This may restart the patient's heart and save the patient's life.

BRIEF SUMMARY

The present description discloses instances of WCD systems, storage media storing programs, and methods, the use of which may help overcome problems and limitations of the prior art.

In embodiments, a WCD system is configured to be worn by a patient who carries a mobile communication device.

The mobile communication device has a user interface that is configured to enable the patient to enter wireless inputs. The WCD system includes a communication module that is configured to establish a local comlink with the mobile communication device. The WCD system also includes a tethered action unit that has a user interface configured to enable the patient to enter action inputs. The WCD system can perform some of its functions in response to the action inputs or to the wireless inputs. Since the wireless inputs can be provided from the mobile communication device instead of the action unit, the patient is less likely to attract attention when entering the action inputs, and thus exhibit better compliance.

In embodiments, a WCD system includes a support structure that is configured to be worn by the patient. A first electronics module is configured to be coupled to the support structure such that, when the support structure is worn by the patient, the first electronics module is substantially located at the lumbar region of the patient. This way, the support structure is less discernible to others, and the patient is less demotivated from wearing it.

BRIEF DESCRIPTION OF THE DRAWINGS

FIG. 11 is a flow diagram showing a process to implement an electrode for use with a medical device, according to embodiments.

FIG. 12 is a flow diagram showing a process of using an electrode with a medical device garment, according to embodiments.

FIG. 13 is a flow diagram showing a process of configuring a support structure for wearable medical device, according to embodiments.

DETAILED DESCRIPTION

Figure 1:
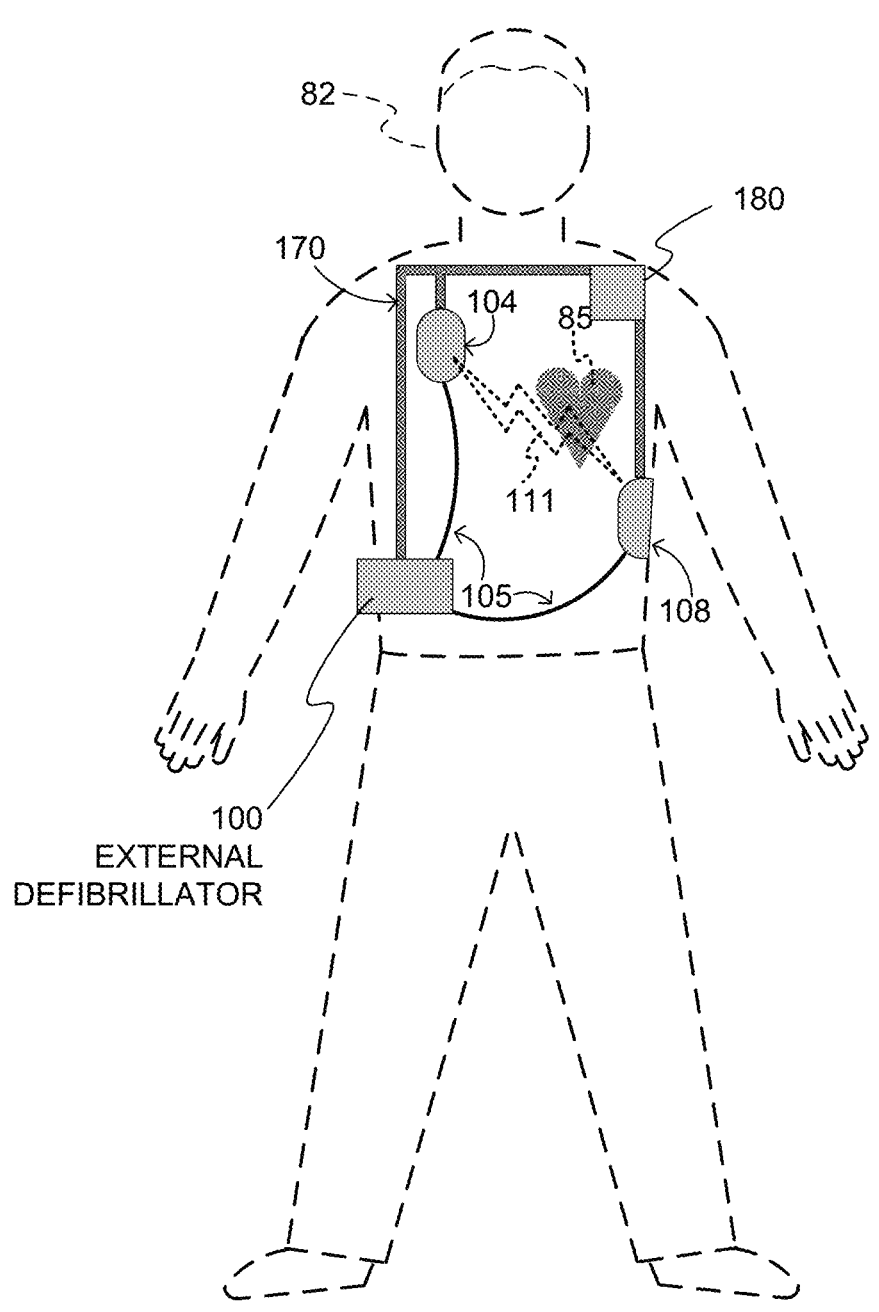
FIG. 1 is a diagram of components of a sample WCD system, made according to embodiments.

A WCD system according to embodiments may protect an ambulatory patient by electrically restarting their heart if needed. Such a WCD system may have a number of components. These components can be provided separately as modules that can be interconnected, or can be combined with other components, and so on.

Successful use of a WCD can depend on the patient's compliance in continuously wearing the WCD, so patients are typically instructed to wear the WCD always except while bathing. Applicants after careful review have appreciated several disadvantages of the some currently available WCDs, which are described below.

Some currently available WCDs use capacitively coupled electrodes to monitor the electrical activity of the patient's heart by sensing the corresponding electric fields that are present on the patient's skin. Such electrodes can have a rigid metal plate with an insulation layer between the plate and patient, which acts as the dielectric between two conductive surfaces to form a capacitor. As the electric field on the skin of the patient changes, it induces a corresponding voltage in the electrode plate without allowing current to flow. The electrodes can be held against the body by a stretchable garment that provides removable hook-and-loop attachments for the electrodes; cabling can be made to the largest possible size of the garment, and patients are expected to loop, wind, or tuck extra cable out of the way of the electrode.

This conventional approach suffers from at least three deficiencies: (1) the electrodes can be uncomfortable to wear for an extended period of time; (2) the acquired ECG signal can be of low quality, especially when the patient is moving; and (3) the electrodes are complex in construction both mechanically and electrically.

Regarding deficiency (1), these electrodes are intended to be held by the garment in physical contact with the skin over the complete surface of the electrode and maintain the same relative position on the skin always. The existing electrodes, being rigid, must be pressed onto the patient with sufficient pressure to establish physical contact between the surface of the electrode and the skin, which can be uncomfortable. In addition, if the patient is lying down or sitting, additional pressure can be applied to one or more of the electrodes, pushing them even harder into the patient's skin. In this conventional approach, not only is there the discomfort of the electrodes pressing into the patient's skin, there can also be skin irritation, sensitivity, or chaffing of the skin caused by or associated with the electrodes. These conditions tend to reduce the patient's compliance in wearing the WCD.

Regarding deficiency (2), capacitive electrodes attempt to maintain the same relative position from the patient's skin at all times. Since the electrodes in the existing WCD are subject to motion on the skin, whether from the patient's own movements (e.g., walking, rolling over in bed, etc.) or from external sources (e.g., riding in an automobile), the noise level of the signal detected by the electrode increases, decreasing the signal quality.

Regarding deficiency (3), the electrodes used in the conventional approach can include a high impedance buffer amplifier in the electrode assembly to improve performance, thus adding requirements for circuitry in the electrode and more complex cabling between the electrode and its associated amplifier. The cabling also causes discomfort and unnecessary alarms, both by pressing into the skin and by working its way under the ECG electrode. For these and other reasons the conventional approach described above can result in lowered patient compliance and in lowered performance of the WCD. Some of the embodiments described below can reduce one or more of the disadvantages described above to improve patient compliance and/or WCD performance.

FIG. 1 depicts a patient 82. Patient 82 may also be referred to as a person and/or wearer, since the patient is wearing components of the WCD system. Patient 82 is ambulatory, which means that, while wearing the wearable portion of the WCD system, patient 82 can walk around and is not necessarily bedridden. While patient 82 may be considered to be also a "user" of the WCD system, this is not a requirement. That is, for example, a user of the WCD may also be a clinician such as a doctor, nurse, emergency medical technician (EMT) or other similarly situated individual (or group of individuals). In some extreme cases a user may be a bystander. The particular context of these and other related terms within this description should be interpreted accordingly.

A WCD system according to embodiments can be configured to defibrillate the patient who is wearing the designated parts of the WCD system. Defibrillating can be by the WCD system delivering an electrical charge to the patient's body in the form of an electric shock. The electric shock can be delivered in one or more pulses.

In particular, FIG. 1 also depicts components of a WCD system made according to embodiments. One such component is a support structure 170 that is wearable by ambulatory patient 82. Accordingly, support structure 170 is configured to be worn by ambulatory patient 82 for at least several hours per day, and for at least several days, even a few months.

It will be understood that support structure 170 is shown only generically in FIG. 1, and in fact partly conceptually. FIG. 1 is provided to illustrate concepts about support structure 170 and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to analogous articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient's body by adhesive material, for example as shown and described in U.S. Pat. No. 8,024,037. Support structure 170 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples.

FIG. 1 shows a sample external defibrillator 100, and sample defibrillation electrodes 104, 108, which are coupled to external defibrillator 100 via electrode leads 105. Defibrillation electrodes 104, 108 can be configured to be worn by patient 82 in a number of ways. For instance, defibrillator 100 and defibrillation electrodes 104, 108 can be coupled to support structure 170, directly or indirectly. In other words, support structure 170 can be configured to be worn by ambulatory patient 82 so as to maintain at least one of electrodes 104, 108 on the body of ambulatory patient 82, while patient 82 is moving around, etc. The electrode can be thus maintained on the body by being attached to the skin of patient 82, simply pressed against the skin directly or through garments, etc. In some embodiments the electrode is not necessarily pressed against the skin but becomes biased that way upon sensing a condition that could merit intervention by the WCD system. In addition, many of the components of defibrillator 100 can be considered coupled to support structure 170 directly, or indirectly via at least one of defibrillation electrodes 104, 108. When defibrillation electrodes 104, 108 make good electrical contact with the body of patient 82, defibrillator 100 can administer, via electrodes 104, 108, a brief, strong electric pulse 111 through the body. Pulse 111 is also known as shock, defibrillation shock, therapy, electrotherapy, therapy shock, etc. Pulse 111 is intended to go through and restart heart 85, in an effort to save the life of patient 82. Pulse 111 can further include one or more pacing pulses of lesser magnitude to simply pace heart 85 if needed, and so on.

A prior art defibrillator typically decides whether to defibrillate or not based on an ECG signal of the patient. However, external defibrillator 100 may initiate defibrillation, or hold-off defibrillation, based on a variety of inputs, with the ECG signal merely being one of these inputs.

A WCD system according to embodiments can obtain data from patient 82. For collecting such data, the WCD system may optionally include at least an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document.

For some of these parameters, device 180 may include one or more sensors or transducers. Each one of such sensors can be configured to sense a parameter of patient 82, and to render an input responsive to the sensed parameter. In some embodiments the input is quantitative, such as values of a sensed parameter; in other embodiments the input is qualitative, such as informing whether or not a threshold is crossed, and so on. Sometimes these inputs about patient 82 are also called physiological inputs. In embodiments, a sensor can be construed more broadly, as encompassing many individual sensors.

Optionally, device 180 is physically coupled to support structure 170. In addition, device 180 may be communicatively coupled with other components that are coupled to support structure 170. Such communication can be implemented by a communication module, as will be deemed applicable by a person skilled in the art in view of this description.

In embodiments, one or more of the components of the shown WCD system may be customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. The measured values of such baseline physiological parameters can be used to customize the WCD system, in order to make its diagnoses more accurate, since the patients' bodies differ from one another. Of course, such parameter values can be stored in a memory of the WCD system, and so on. Moreover, a programming interface can be made according to embodiments, which receives such measured values of baseline physiological parameters. Such a programming interface may input automatically in the WCD system these, along with other data.

Figure 2:
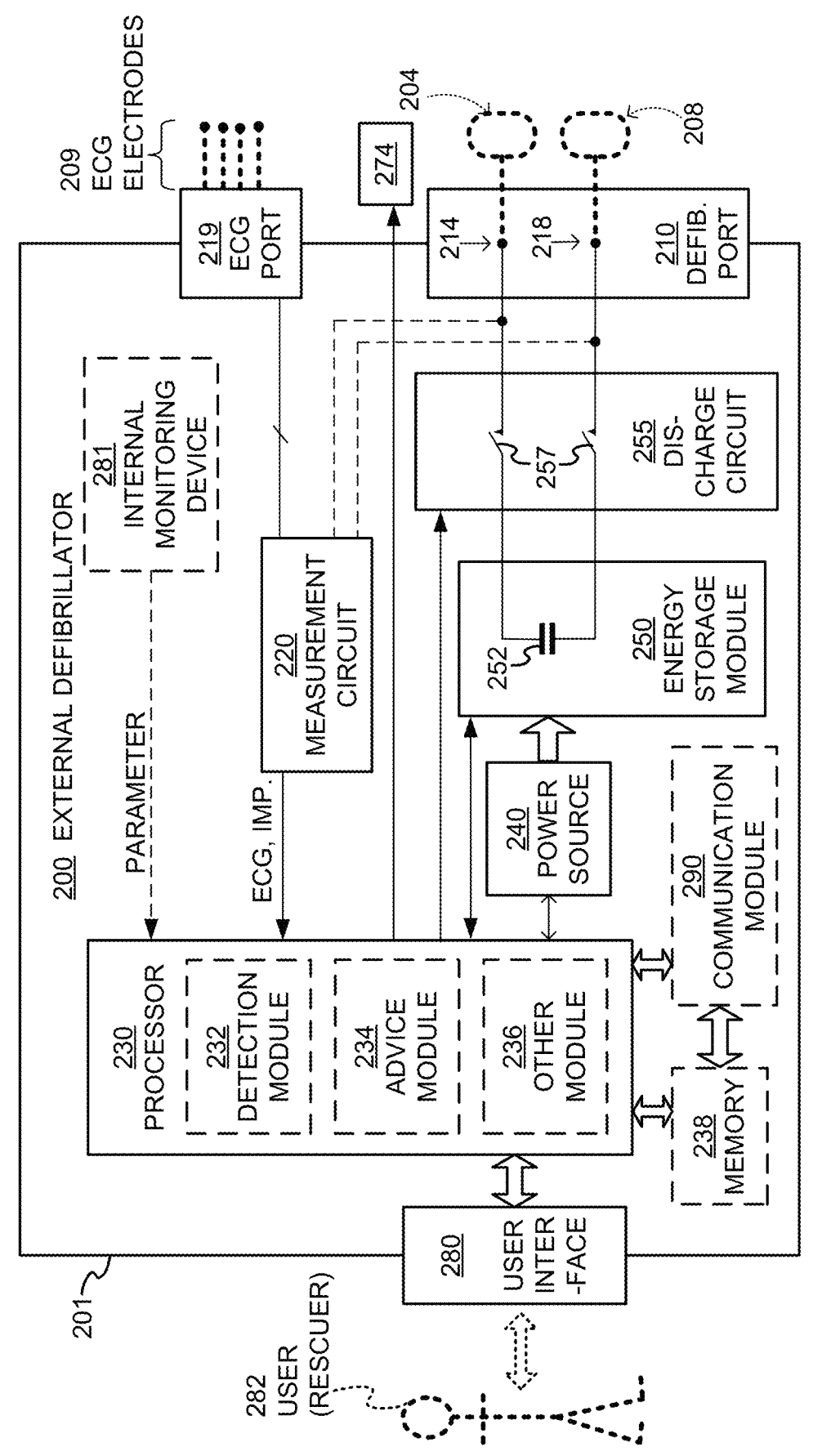
FIG. 2 is a diagram showing sample components of an external defibrillator, such as the one belonging in the system of FIG. 1, and which is made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended for a patient who would be wearing it, such as ambulatory patient 82 of FIG. 1. Defibrillator 200 may further include a user interface 280 for a user 282. User 282 can be patient 82, also known as wearer 82. Or, user 282 can be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible or tactile, for communicating to a user by outputting images, sounds or vibrations. Images, sounds, vibrations, and anything that can be perceived by user 282 can also be called human-perceptible indications (HPIs). There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds and/or words to warn bystanders, etc.

User interface 280 may further include input devices for receiving inputs from users. Such input devices may include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 may include one or more sensors as described above.

Patient parameters may include patient physiological parameters. Patient physiological parameters may include, for example and without limitation, those physiological parameters that can be of any help in detecting by the WCD system whether or not the patient needs a shock or other intervention or assistance. Patient physiological parameters may also optionally include the patient's medical history, event history and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include one or more electrodes to detect ECG data, a perfusion sensor, a pulse oximeter, a device for detecting blood flow (e.g., a Doppler device), a sensor for detecting blood pressure (e.g., a cuff), an optical sensor, illumination detectors and sensors perhaps working together with light sources for detecting color change in tissue, a motion sensor, a device that can detect heart wall movement, a sound sensor, a device with a microphone, an SpO2 sensor, and so on. In view of this disclosure, it will be appreciated that such sensors can help detect the patient's pulse, and can therefore also be called pulse detection sensors, pulse sensors, and pulse rate sensors and or as taught in U.S. Pat. No. 8,135,462, which is hereby incorporated by reference in its entirety. In addition, a person skilled in the art may implement other ways of performing pulse detection.

In some embodiments, the local parameter is a trend that can be detected in a monitored physiological parameter of patient 282. A trend can be detected by comparing values of parameters at various times over short and long terms. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from SpO2, CO2, or other parameters such as those mentioned above, f) respiratory function, respiratory rate, etc.; g) motion, level of activity; and so on. Once a trend is detected, it can be stored and/or reported via a communication link, along perhaps with a warning if warranted. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may thus include a motion detector. In embodiments, a motion detector can be implemented within monitoring device 180 or monitoring device 281. Such a motion detector can be made in many ways as is known in the art, for example by using an accelerometer. In this example, a motion detector 287 is implemented within monitoring device 281.

A motion detector of a WCD system according to embodiments can be configured to detect a motion event. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed, if monitoring device 180 or 281 includes a GPS location sensor as per the above, and if it is presumed that the patient is wearing the WCD system.

Defibrillator 200 typically includes a defibrillation port 210, which can be a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, e.g., a 12-lead signal, or a signal from a different number of leads, especially if they make good electrical contact with the body of the patient and in particular with the skin of the patient. Sensing electrodes 209 can be attached to the inside of support structure 170 for making good electrical contact with the patient, similarly with defibrillation electrodes 204, 208.

Optionally a WCD system according to embodiments also includes a fluid that it can deploy automatically between the electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel, so that it does not flow away, after being deployed, from the location it is released near the electrode. The fluid can be used for both defibrillation electrodes 204, 208, and for sensing electrodes 209.

The fluid may be initially stored in a fluid reservoir, not shown in FIG. 2. Such a fluid reservoir can be coupled to the support structure. In addition, a WCD system according to embodiments further includes a fluid deploying mechanism 274. Fluid deploying mechanism 274 can be configured to cause at least some of the fluid to be released from the reservoir, and be deployed near one or both of the patient locations to which electrodes 204, 208 are configured to be attached to the patient. In some embodiments, fluid deploying mechanism 274 is activated prior to the electrical discharge responsive to receiving activation signal AS from a processor 230, which is described more fully later in this document.

In some embodiments, defibrillator 200 also includes a measurement circuit 220, as one or more of its sensors or transducers. Measurement circuit 220 senses one or more electrical physiological signals of the patient from sensor port 219, if provided. Even if defibrillator 200 lacks sensor port 219, measurement circuit 220 may optionally obtain physiological signals through nodes 214, 218 instead, when defibrillation electrodes 204, 208 are attached to the patient. In these cases, the input reflects an ECG measurement. The patient parameter can be an ECG, which can be sensed as a voltage difference between electrodes 204, 208. In addition, the patient parameter can be an impedance, which can be sensed between electrodes 204, 208 and/or between the connections of sensor port 219 considered pairwise. Sensing the impedance can be useful for detecting, among other things, whether these electrodes 204, 208 and/or sensing electrodes 209 are not making good electrical contact with the patient's body. These patient physiological signals may be sensed when available. Measurement circuit 220 can then render or generate information about them as inputs, data, other signals, etc. More strictly speaking, the information rendered by measurement circuit 220 is output from it, but this information can be called an input because it is received as an input by a subsequent device or functionality.

Defibrillator 200 also includes a processor 230. Processor 230 may be implemented in a number of ways. Such ways include, by way of example and not of limitation, digital and/or analog processors such as microprocessors and Digital Signal Processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 may include, or have access to, a non-transitory storage medium, such as memory 238 that is described more fully later in this document. Such a memory can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as inputs, data that reflect values, or other signals, may be used by the VF detector to determine whether the patient is experiencing VF. Detecting VF is useful, because VF typically results in SCA. Detection module 232 can also include a Ventricular Tachycardia (VT) detector, and soon.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments and determining whether or not a shock criterion is met. The determination can be made from a rhythm analysis of the captured ECG signal or otherwise.

In some embodiments, when the determination is to shock, an electrical charge is delivered to the patient. Delivering the electrical charge is also known as discharging and shocking the patient. As mentioned above, such can be for defibrillation, pacing, and so on.

Processor 230 can include additional modules, such as other module 236, for other functions. In addition, if internal monitoring device 281 is indeed provided, processor 230 may receive its inputs, etc.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or stored there after it is received by defibrillator 200.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy-storing capacitor, and so on. Appropriate components may be included to provide for charging or replacing power source 240. In some embodiments, power source 240 is controlled and/or monitored by processor 230.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

A decision to shock can be made responsive to the shock criterion being met, as per the above-mentioned determination. When the decision is to shock, processor 230 can be configured to cause at least some or all of the electrical charge stored in module 250 to be discharged through patient 82 while the support structure is worn by patient 82, so as to deliver a shock 111 to patient 82.

For causing the discharge, defibrillator 200 moreover includes a discharge circuit 255. When the decision is to shock, processor 230 can be configured to control discharge circuit 255 to discharge through the patient at least some of all of the electrical charge stored in energy storage module 250. Discharging can be to nodes 214, 218, and from there to defibrillation electrodes 204, 208, so as to cause a shock to be delivered to the patient. Circuit 255 can include one or more switches 257. Switches 257 can be made in a number of ways, such as by an H-bridge, and so on. Circuit 255 could also be controlled via user interface 280.

A time waveform of the discharge may be controlled by thus controlling discharge circuit 255. The amount of energy of the discharge can be controlled by how much energy storage module has been charged, and also by how long discharge circuit 255 is controlled to remain open.

Defibrillator 200 can optionally include a communication module 290, for establishing one or more wired or wireless communication links with other devices of other entities, such as a remote assistance center, Emergency Medical Services (EMS), and so on. The communication links can be used to transfer data and commands. The data may be patient data, event information, therapy attempted, CPR performance, system data, environmental data, and so on. For example, communication module 290 may transmit wirelessly, e.g., on a daily basis, heart rate, respiratory rate, and other vital signs data to a server accessible over the internet, for instance as described in US 20140043149. This data can be analyzed directly by the patient's physician and can also be analyzed automatically by algorithms designed to detect a developing illness and then notify medical personnel via text, email, phone, etc. Module 290 may also include such interconnected sub-components as may be deemed necessary by a person skilled in the art, for example an antenna, portions of a processor, supporting electronics, outlet for a telephone or a network cable, etc. Defibrillator 200 can optionally include other components.

Figure 3:
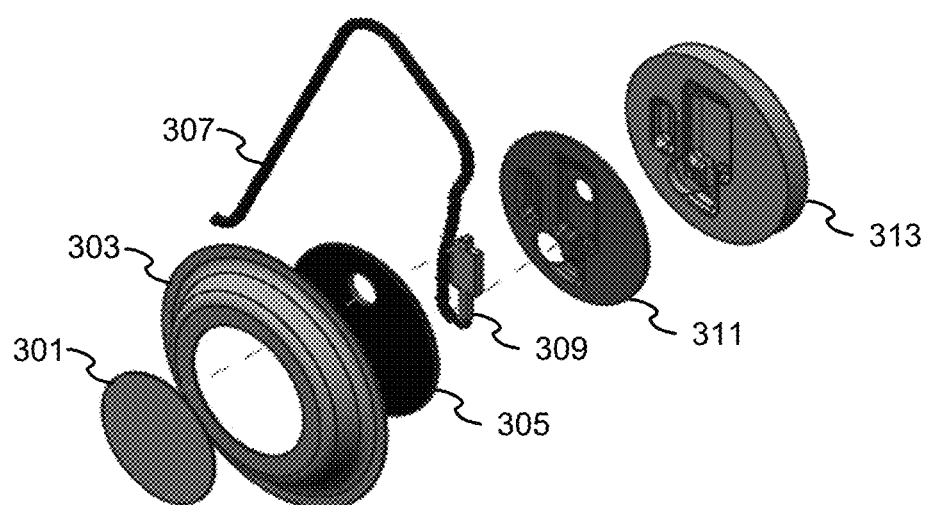
FIG. 3 is a diagram showing an electrode assembly, according to embodiments.

FIG. 3 is a diagram showing an electrode assembly, which can be used with a wearable medical device, according to embodiments. For example, some embodiments can be used to implement one or more of the ECG electrodes 209 (FIG. 2). In some embodiments the electrode includes a "pillow" as a suspension system that allows the electrode surface to remain in unmoving contact with the skin despite pressure variations of the garment and movement of the skin relative to the garment.

Embodiments of the electrode assembly include a conductive electrode 301, an elastic cover 303, a mounting substrate 305, a shielded cable 307, a resistive element 309 (for embodiments used with providing high voltage patient therapy), a shield or cover 311, and a pillow 313. Embodiments of pillow 313 include a soft element, for example a piece of foam (e.g., made from open-cell urethan foam, open-cell polyester foam, spacer mesh/3-D resilient fabric, etc.), which supports electrode 301 and allows it to translate sideways as well as normal/anti-normal to its face as the skin moves. Other embodiments include, optionally, a cover 303 which can be implemented as an elastic cover that protects the inner components of the electrode assembly. In yet other embodiments, the electrode assembly optionally also includes mounting substrate 305 implemented using an insulator that supports the electrode 301 and prevents arcing from the electrode 301 to other circuitry of the medical device coupled to the electrode assembly. Further, in some such high voltage therapy embodiments, the electrode assembly can include defibrillation protection resistive element 309 (which can be a resistor) that is coupled to the electrode 301 via cable 307 (which in some embodiments cable 307 is shielded). In still other embodiments, shield 311 acts both as an electric field shield (through being coated on the outside with a conductive coating) and as an encapsulant shell over resistive element 309 in embodiments in which at least a portion of the electrode electronics is encapsulated with potting material (e.g., potted to protect the electrode assembly during washing).

In some embodiments with resistive element 309, one lead of the element is electrically connected to electrode 301 and the other lead is electrically connected to monitoring circuitry of a WCD via shielded cable 307. These embodiments are different from some conventional approaches in which a resistor is part of the cabling of a professional ECG monitoring cable and integrated into the electrode itself. In some embodiments, resistive element 309 has a value of 5OKO, and can range from IKO-IOOKO in other embodiments.

Figure 4:
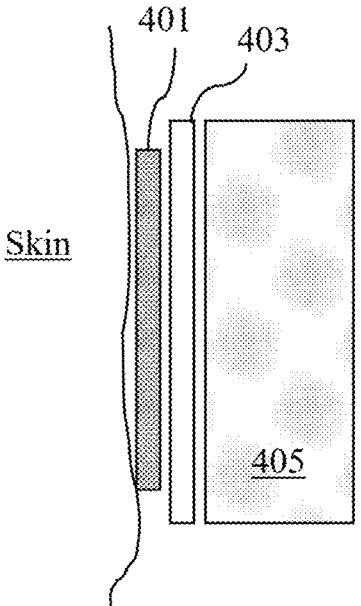
FIG. 4 is a diagram schematically showing an electrode assembly with a moisture barrier, according to embodiments.

FIG. 4 is a diagram schematically showing an electrode assembly with a moisture barrier, according to embodiments. Some of these embodiments can include covers, shielded cables, mounting substrates, protection resistors, and shielding as described above in conjunction with FIG. 3, which are not shown in FIG. 4.

Embodiments of the electrode assembly include an electrode 401, a moisture barrier 403, and a mounting structure 405. In some embodiments, mounting structure 405 includes a "pillow" structure as described above. Embodiments of electrode 401 and moisture 403 are described in more detail below.

In some embodiments, electrode 401 includes a metallic silver surface for contacting the patient's skin. Metallic silver has excellent conductivity, very low skin impedance, and provides a good ionic-to-electronic conversion path for electrical signals moving from the ionic conduction of the body to the metallic conduction path of an electrical device. In embodiments, this helps ensure detection with low signal noise resulting in a good quality ECG signal output from electrode 401. In some embodiments, the surface of the silver material is treated or processed to improve comfort against the skin. For example, in some embodiments the metallic silver surface is textured with a bead-blast and/or formed with tiny holes which allow the skin to breathe. However, too many holes or holes being too large can cause patient discomfort from drying out and/or scraping the patient's skin. In some embodiments, the silver material is made with substantially the same thickness as the surrounding covering fabric and mounted to a semi-rigid backer to provide a "flush" mount in which the fabric surface and the electrode surface are the same height with no step left to cause irritation. Alternative materials such as, for example, silver alloys are used instead of metallic silver in other embodiments. In some embodiments, the electrode surface for contacting the skin is approximately circular with a diameter of about 1.04" but can range from 0.75" to 1.25" in other embodiments. In still other embodiments, the size of the electrode can be reduced depending on the application and how much the electrode moves when the patient is wearing the support structure along with the electrodes. For example, an electrode that has substantially no movement when the support structure is worn can be 0.5" in diameter or even smaller.

In some embodiments, electrode 401 is implemented as a fabric electrode formed using thread made from conductive material, or thread made with a conductive coating, and/or a thread formed from conductive and non-conductive fibers.

In some embodiments, moisture barrier 403 is implemented as a moisture-impermeable barrier applied on or attached to the back side of electrode 401 (i.e., the side away from the skin). Some such embodiments can be advantageously used with electrode 401 made with fabric or porous materials. For example, WCDs commonly have a garment or harness with ECG electrodes positioned so that they are located at selected positions on the patient's body while the garment/harness is being worn. Some ECG monitoring garments are made with textile or fabric electrodes incorporated into the garment. For example, the textile electrode may be conductive thread woven into the garment. These textile electrodes are designed as "dry" electrodes (see for example US Pat. App. Pub. No. 20140206948, paragraph [0048]).

After careful investigation and analysis, applicants have appreciated that when using porous or fabric electrodes, enough moisture will evaporate from a wearer's skin to generate higher skin impedances that can degrade the quality of the sensed ECG. Consequently, dry fabric electrodes may not have sufficient performance for some applications that require a very high-quality ECG signal, such as a WCD. In response to this finding, Applicants implemented embodiments of an electrode assembly with a vapor-impermeable and/or moisture barrier such as moisture barrier 403 that can improve moisture trapping to provide good electrical contact between the electrode and the skin (i.e., resulting in good ECG detection) while allowing air flow through the permeable electrode to improve comfort.

In some embodiments, moisture barrier 403 is a water impermeable film or layer that is disposed "behind" electrode 401. That is, placed on the side of electrode 401 that is not touching the patient's skin. This side is also referred to herein as the "barrier side" of electrode 401. In some embodiments barrier 403 is a fabric layer made of a water impermeable thread such as nylon or polyester with a dense weave to restrict permeability. In other embodiments, barrier 403 is a flexible resilient material such as silicone. In other embodiments, barrier 403 is a breathable but waterproof material such as Gortex®. In other embodiments, barrier 403 is a more rigid material such as a plastic (e.g., polyethylene, polypropylene, acrylic, polycarbonate, etc.). In other embodiments, barrier 403 is a coating or liquid.

According to various embodiments, barrier 403 is attached to electrode 401 by an adhesive, sewing/stitching, or hook/loop, or other fastening technologies. In other embodiments, barrier 403 is implemented by applying or spraying a water repellent coating on electrode 401.

In still other embodiments used with garments or harnesses, a pouch or pocket is disposed behind each electrode in which a water impermeable shield (e.g., barrier 403) is placed. This shield can be a plastic sheet sized and shaped to securely fit in the pocket, similar to a collar stay for a shirt. In some embodiments the pocket is designed to allow barrier 403 to be removable, while in other embodiments, the pocket is "closed" after placement of the vapor barrier so that the vapor barrier is permanently attached to the fabric electrode.

In some embodiments, barrier 403 is designed to stiffen or increase rigidity of a fabric electrode "assembly" (which includes the moisture barrier) to help the fabric electrode assembly from rolling or folding while worn by the patient. This feature can help maintain the amount of surface area of the fabric electrode contacting the patient's skin. In some embodiments, substantially all of the "barrier side" of a fabric electrode 401 is covered by barrier 403, while in other embodiments one or more portions of the "barrier side" of the fabric electrode is not covered by barrier 403.

Figure 5:
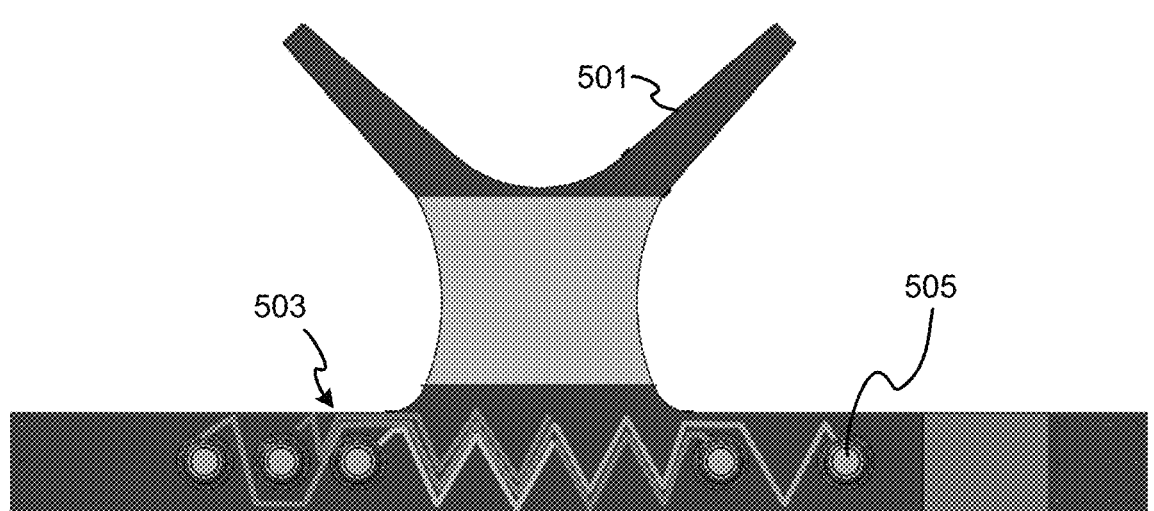
FIG. 5 is a diagram showing a WCD garment with wiring, according to embodiments.

FIG. 5 is a diagram showing a WCD garment 501 with wiring 503 to sensors 505 (e.g., electrodes described above), according to embodiments. In some embodiments, wiring 503 is configured to stretch with a fabric garment with no or minimal distortion. This feature can advantageously be used to prevent wiring 503 from getting tangled or overlaid upon itself, which can result in "lumps" in garment 501 that can cause patient discomfort. In some embodiment, wiring 503 is configured in a pattern that uses vertical convolutions (e.g., a triangular zig-zag patterns, sinusoidal wave patterns, etc.) to allow the fabric to stretch horizontally without causing the wiring to tighten. In some embodiments, garment 501 and/or wiring 503 have attachment points which form the points of each zigzag. In FIG. 5, wires of wiring 503 are attached to garment 501 at each point where the wires changes direction. Having wiring 503 attached in this fashion without extra slack ensures that the wires do not overlay each other.

Figure 6:
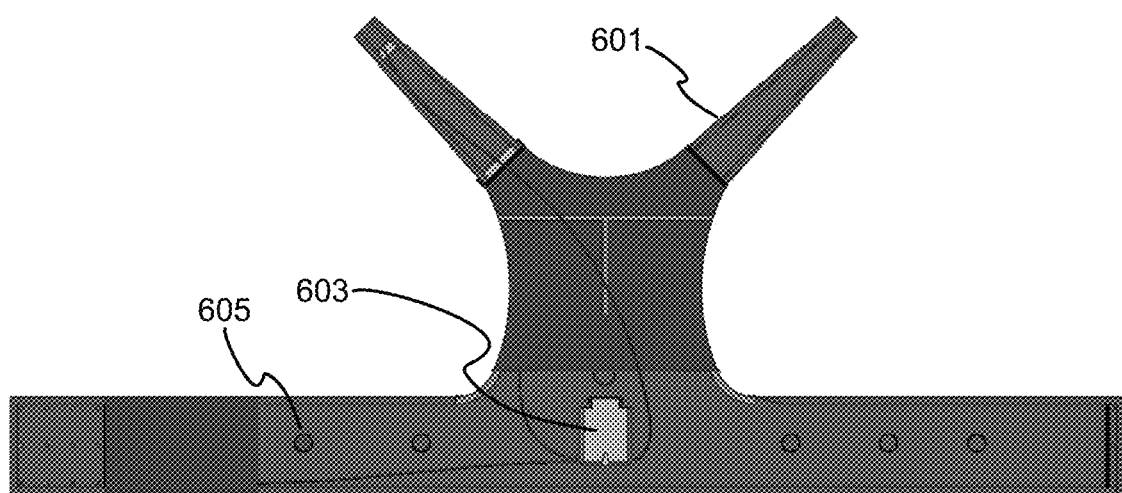
FIG. 6 is a diagram showing a WCD garment with a hermetic connector and electrode status indicator according to embodiments.

FIG. 6 is a diagram showing a garment 601 with a connector 603 and electrode status indicator 605 according to embodiments. Some embodiments of garment 601 can be advantageously used in WCDs.

In some embodiments, connector 603 is a washable hermetic connector that is permanently incorporated into garment 601 for connection to wiring (such as wiring 503 of FIG. 5) attached to the garment. Some such embodiments can advantageously enable all of the connections to sensors in garment 601 (e.g., ECG electrodes of FIGS. 3-5) to be connected to monitoring circuitry at once, in which the connector 603 is attached to the fabric of the garment 601 and the wiring (which can be inside or integrated into the garment). In embodiments, connector 603 is hermetically sealed to allow washing without degradation of its electrical function. Additionally, in some embodiments a module (not shown) configured with the signal conditioning functionality for the ECG signals is incorporated into the garment. In still other embodiments, the defibrillation electrodes are also permanently integrated into the garment.

In some embodiments, a small indicator 605 (e.g., an LED), is coupled with each ECG electrode assembly. When the WCD system detects fault such as, for example, that an ECG electrode has too high impedance due to skin dryness, the system is configured to indicate which electrode is at issue by activating the indicator 605. As shown in FIG. 6, the outside of the garment 601 has a small red LED is used to implement indicator 605 to visibly indicate which electrode is at fault. These embodiments can advantageously enable a person wearing the garment to determine that all of their electrodes are functioning properly and if not all functioning properly to determine with electrode or electrodes are not. Alternately, indicator 605 could be a single or multiple LED's located at a single location that would be more easily viewable by the patient. For example, indicator 605 a single LED at the main garment closure.

Figure 7:
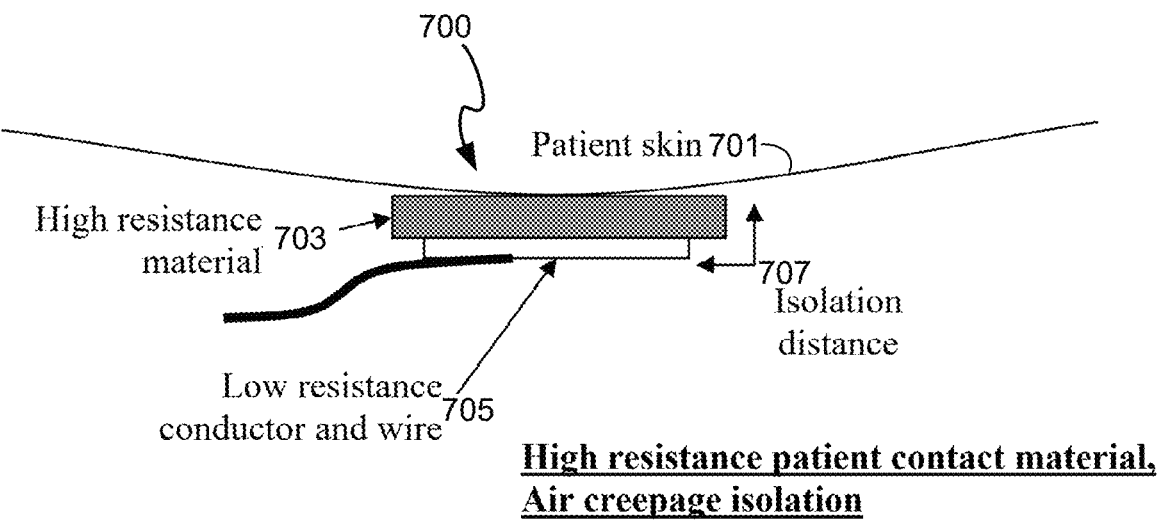
FIG. 7 is a diagram schematically showing an electrode assembly disposed on a patient's skin, according to embodiments.

FIG. 7 is a diagram schematically showing an electrode assembly 700 disposed on a patient's skin 701, according to embodiments. In some embodiments, a high-impedance material 703 is used for the electrode material and the resistance is set by the thickness of that material to provide defibrillation protection instead of a resistor (e.g., resistive element 309 in FIG. 3). For example, in some embodiments high-impedance material 703 have consistent high resistance in the 1-IOOKO range such as, for example, carbon particle filled polymers, fine metal particle filled polymers, or metal oxide particle filled polymers.

In addition, in some embodiments, electrode assembly 700 is structured to maintain an isolation or creepage distance 707 between the patient's skin and the conductive wiring 705 (including conductive plates, signal lines, cabling, wires, etc.). For example, conductive wiring 705 can be used to connect the electrode to other circuitry of the WCD system. When high voltage is present on the patient's skin, a low-resistance conductive path (i.e., the monitor connection, absent any protective resistance) between the electrode and the skin may be susceptible to arcing during the administration of a shock. Some embodiments provide air creepage distance 707 across the high-resistance material to prevent arcing during defibrillation. These embodiments that maintain a minimum creepage distance can be advantageously used in WCD systems in which the voltage at the outside of the electrode assembly during defibrillation is relatively low (e.g., below 1000 volts) so that additional protection resistors are eliminated.

Figure 8:
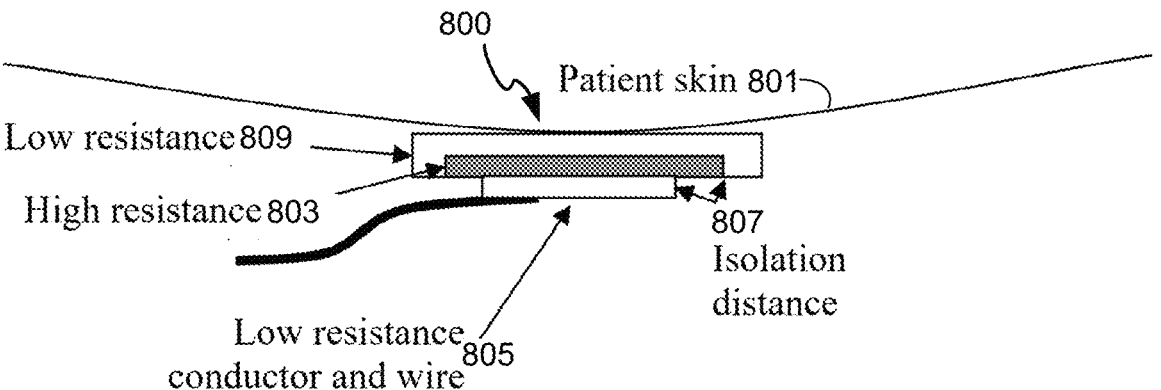
FIG. 8 is a diagram schematically showing an electrode assembly disposed on a patient's skin, according to other embodiments.

FIG. 8 is a diagram schematically showing another electrode assembly 800 disposed on a patient's skin 801, according to other embodiments. In some embodiments of FIG. 8, a two-layer electrode is used, in which a first layer 809 is a relatively thinner layer of lower-impedance material (e.g., material comprising silver) interfaced to the patient skin, and a second layer 805 is of higher-impedance material (e.g., carbon particle filled polymers, fine metal particle filled polymers, or metal oxide particle filled polymers) to provide the needed resistance by its thickness. In addition, as in some of the embodiments of FIG. 7), electrode assembly 800 is structured to maintain an isolation or creepage distance 807 between the patient's skin and the conductive wiring 805 to prevent arcing during defibrillation.

Figure 9:
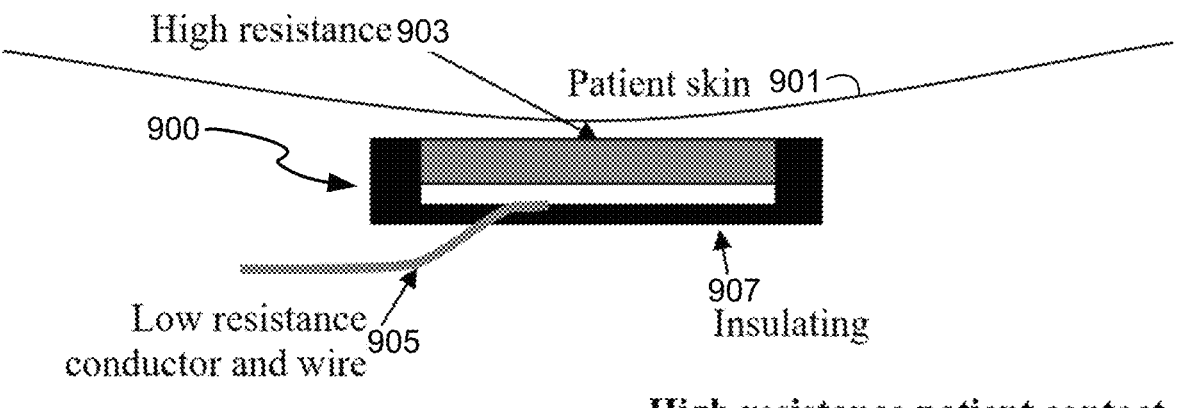
FIG. 9 is a diagram schematically showing an electrode assembly disposed on a patient's skin, according to still other embodiments.

FIG. 9 is a diagram schematically showing an electrode assembly 900 disposed on a patient's skin 901, according to still other embodiments. According to embodiments of electrode assembly 900, along with a relatively high resistance material 903 (similar to high resistance material 703 of FIG. 7) and a conductor 905, an insulating material 907 is used to maintain a minimum creepage isolation to prevent arcing across the high-resistance surface. In some embodiments, insulating material 907 partially surrounds high-resistance material 903, except for the surface of high-resistance material 903 facing patient's skin 901.

Figure 10:
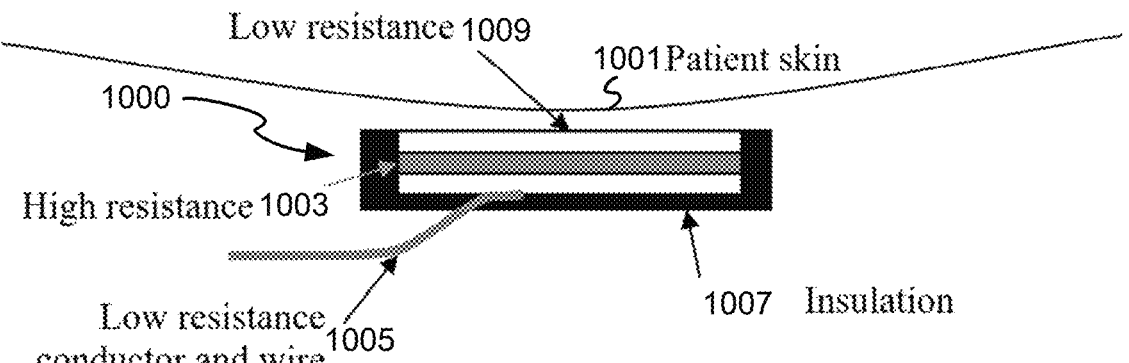
FIG. 10 is a diagram schematically showing an electrode assembly disposed on a patient's skin, according to other embodiments.

FIG. 10 is a diagram schematically showing a two-layer electrode assembly 1000 disposed on a patient's skin 1001, according to still other embodiments. According to embodiments, a two-layer electrode assembly (similar to the two-layer electrode assembly 800 of FIG. 8) comprises a relatively high resistance material 1003 (similar to high resistance material 803 of FIG. 8), a conductor 1005 and a low resistance material 1009 (similar to low resistance material 809 of FIG. 8), an insulating material 1007 is used to maintain a minimum creepage isolation to prevent arcing across the high-resistance surface. In some embodiments, insulating material 1007 partially surrounds layers 1003 and 1009, except for the surface of low resistance material 1009 facing patient's skin 1001.

The devices and/or systems mentioned in this document may perform functions, processes, acts, operations, actions and/or methods. These functions, processes, acts, operations, actions and/or methods may be implemented by one or more devices that include logic circuitry. A single such device can be alternately called a computer, and so on. It may be a standalone device or computer, such as a general-purpose computer, or part of a device that has and/or can perform one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

Moreover, methods and algorithms are described below. These methods and algorithms are not necessarily inherently associated with any particular logic device or other apparatus. Rather, they are advantageously implemented by programs for use by a computing machine, such as a general-purpose computer, a special purpose computer, a microprocessor, a processor such as described elsewhere in this document, and so on.

This detailed description may include flowcharts, display images, algorithms, and symbolic representations of program operations within at least one computer readable medium. An economy may be achieved in that a single set of flowcharts can be used to describe both programs, and also methods. So, while flowcharts describe methods in terms of boxes, they may also concurrently describe programs.

FIG. 11 is a flow diagram showing a process 1100 to implement one or more electrodes for use with a medical device (e.g., wearable monitoring and therapy devices), according to embodiments. For example, the electrodes may be ECG electrodes similar to ECG electrode 209 (FIG. 2).

In an operation 1102, a permeable electrode is formed. For example, in some embodiments the permeable electrode can be a fabric electrode or a metallic electrode with pores, as previously described in conjunction with FIG. 4.

In an operation 1104, a moisture barrier is formed and positioned on, adjacent, or near the permeable electrode to reduce drying out of the permeable electrode. In some embodiments, the moisture barrier can be formed from a flexible sheet of plastic, a solution applied to the electrode, a densely woven piece of fabric, etc., as previously described in conjunction with FIG. 4. In embodiments, the moisture barrier is located or positioned on the side of the electrode that is opposite of the side intended to contact the patient's skin.

In an operation 1106, the electrode and moisture barrier formed in operations 1102 and 1104 are incorporated into a garment to be worn by a user. For example, in some embodiments the garment is a garment or support structure used in a WCD or wearable monitoring device, as described above in conjunction with FIGS. 1, 2 5, and 6.

In an operation 1108, an interface if formed to communicatively couple the electrode formed in operation 1102 with a processor or other monitoring circuitry. For example, the interface can couple the electrode to a defibrillator similar to defibrillator 200 (FIG. 2). In some embodiments, the interface is implemented using conductive wiring such as conductors 705 or 805 of FIGS. 7 and 8, respectively. In other embodiments, the interface can be a wireless interface. In still other embodiments, the interface can be a port similar to ECG port 219 (FIG. 2).

FIG. 12 is a flow diagram showing a process 1200 of implementing one or more electrodes with a medical device garment, according to other embodiments. For example, the electrodes may be ECG electrodes similar to ECG electrode 209 (FIG. 2).

In an operation 1202, a permeable electrode is formed from a conductive fabric. For example, in some embodiments the permeable electrode can be a fabric electrode as previously described in conjunction with FIG. 4.

In an operation 1204, the at least one permeable fabric electrode is incorporated into a garment to be worn by a user. In some embodiments, the fabric electrode can be woven into the garment as part of the garment manufacturing process. In some embodiments the garment is a garment or support structure used in a WCD or wearable monitoring device, as described above in conjunction with FIGS. 1, 2 5, and 6.

In an operation 1206, a moisture barrier is formed and positioned on, adjacent, or near the at least one permeable electrode to reduce drying out of the permeable electrode. In some embodiments, the moisture barrier can be formed from a flexible sheet of plastic, a solution applied to the electrode, a densely woven piece of fabric, etc., as previously described in conjunction with FIG. 4. In embodiments, the moisture barrier is located or positioned on the side of the electrode that is opposite of the side intended to contact the patient's skin.

In an operation 1208, the at least one electrode is interconnected to a processor or other monitor to enable a signal received by the electrode to be provided to the processor or monitor. For example, the electrode is interconnected to a defibrillator similar to defibrillator 200 (FIG. 2) using conductive wiring such as conductors 705 or 805 of FIGS. 7 and 8, respectively. In other embodiments, the interconnection can be implemented using a wireless connection. In still other embodiments, the at least one electrode can be interconnected to the processor or other monitor through a port similar to ECG port 219 (FIG. 2).

FIG. 13 is a flow diagram showing a process 1300 of configuring a support structure for wearable medical device with one or more ECG electrodes for use by a patient, according to embodiments. For example, in some embodiments the ECG electrodes are configured on the support structure in a manner similar to the configuration of ECG electrode 209 (FIG. 2).

In an operation 1302, a support structure is configured to be worn by a patient. In some embodiments the support structure used in a WCD or other wearable monitoring device, as described above in conjunction with FIGS. 1, 2 5, and 6. In configuring the support structure for the patient, the sizing, materials, arrangement and/or attachment of straps and wiring, etc. can be adjusted to improve comfort for the patient.

In an operation 1304, the support structure is configured with at least one permeable ECG electrode. For example, in some embodiments the permeable ECG electrode can be a fabric electrode or a metallic electrode with pores, as previously described in conjunction with FIG. 4.

In an operation 1306, the permeable ECG electrode is configured with a moisture barrier. In some embodiments, the moisture barrier is formed and positioned on, adjacent, or near the at least one permeable electrode to reduce drying out of the permeable electrode. In some embodiments, the moisture barrier can be formed as part of the electrode (e.g., the previously described processes of coating, densely weaving, sewing, etc. the moisture barrier to the electrode). In other embodiments, the moisture barrier is configured by providing a separate shield that is attached or fitted to the support structure so as to be properly positioned relative to the permeable ECG electrode to reduce evaporation. For example, in some embodiments the support structure has a pocket located adjacent to the permeable ECG electrode in which a plastic shield is placed. In other embodiments, the shield may be attached to the support structure using other attachment mechanisms, such as hook and loop, snaps, etc.

In the methods described above, each operation can be performed as an affirmative step of doing, or causing to happen, what is written that can take place. Such doing or causing to happen can be by the entire system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description. Plus, any reference to any prior art in this description is not, and should not be taken as, an acknowledgement or any form of suggestion that such prior art forms parts of the common general knowledge in any country or any art.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In this document, the phrases "constructed to" and/or "configured to" denote one or more actual states of construction and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Any and all parent, grandparent, great-grandparent, etc. patent applications, whether mentioned in this document or in an Application Data Sheet (ADS) of this patent application, are hereby incorporated by reference herein, including any priority claims made in those applications and any material incorporated by reference, to the extent such subject matter is not inconsistent herewith.

In this description a single reference numeral may be used consistently to denote a single aspect, component, or process. Moreover, a further effort may have been made in the drafting of this description to choose similar though not identical reference numerals to denote versions or embodiments of an aspect, component or process that are the same or possibly different. Where made, such a further effort was not required, but was nevertheless made gratuitously to accelerate comprehension by the reader. Even where made in this document, such an effort might not have been made completely consistently throughout the many versions or embodiments that are made possible by this description. Accordingly, the description controls. Any similarity in reference numerals may be used to confirm a similarity in the text, or even possibly a similarity where express text is absent, but not to confuse aspects where the text or the context indicates otherwise.

The claims of this document define certain combinations and subcombinations of elements, features and steps or operations, which are regarded as novel and non-obvious. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that it can have one or more of this component or item.

What is claimed is:

1. A Wearable Cardioverter Defibrillator (WCD) system, the WCD system comprising:
   a support structure configured to be worn by a patient;
   a power source configured to store electrical charge;
   a discharge circuit coupled to the power source;
   one or more electrode assemblies, each electrode assembly of the one or more electrode assemblies, having an electrode, the electrode having at least a skin-facing surface and a non-skin-facing surface, wherein the electrode of each electrode assembly comprises a plurality of layers, each layer of the plurality of layers having an impedance depending on thickness and material of the layer, and wherein the electrode comprises insulating material at least partially surrounding the plurality of layers at least on two sides except for the skin-facing surface of the electrode;
   wiring comprising one or more wires, wherein the wiring is configured to couple the one or more electrode assemblies and one or more processors, wherein the wiring is configured to stretch with the support structure, and wherein a creepage distance is maintained across the plurality of layers using the insulating material across each of the plurality of layers except the layer having the skin-facing surface, to prevent arcing in the one or more electrode assemblies during defibrillation;
   a plurality of electrode status indicators, wherein each electrode status indicator of the plurality of electrode status indicators is proximate to an electrode assembly of the one or more electrode assemblies and is configured to activate when the WCD system detects a fault; and the one or more processors configured to receive an electrocardiogram (ECG) signal from the one or more electrode assemblies, wherein the one or more processors, based on the received ECG signal, make a shock decision or a no shock decision, and wherein responsive to the shock decision, a shock process is initiated to cause the discharge circuit and the power source to enable, at least, a portion of electrical charge stored in the power source to be delivered to the patient, and responsive to the no shock decision, the discharge circuit and the power source are controlled to prevent delivery of the electrical charge stored in the power source to the patient.

2. The WCD system of claim 1, wherein the wiring is configured into an alternating pattern such that stretching the support structure elongates the wiring without distorting the wiring.

3. The WCD system of claim 2, wherein the alternating pattern is a triangular zig-zag pattern, a substantially sinusoidal wave pattern, or a combination thereof.

4. The WCD system of claim 1, wherein the one or more wires do not overlay each other.

5. The WCD system of claim 1, wherein the moisture barrier is located on or adjacent to the non-skin-facing surface of the electrode.

6. The WCD system of claim 1, wherein the wiring is configured to allow a fabric garment to stretch without distortion.

7. The WCD system of claim 1, wherein the WCD system further comprises one or more attachment points configured to connect the wiring to the support structure where the one or more wires change direction.

8. The WCD system of claim 7, wherein the one or more attachment points secure the one or more wires to the support structure without slack.

9. The WCD system of claim 1, further comprising a connector configured to connect the wiring and the electrode assembly.

10. The WCD system of claim 9, wherein the connector is a washable hermetic connector.

11. The WCD system of claim 1, wherein the electrode comprises a permeable electrode.

12. The WCD system of claim 1, wherein the fault is high impedance of an electrode due to skin dryness.

13. The WCD system of claim 1, wherein the plurality of electrode status indicators are light emitting diodes (LEDs).

14. The WCD system of claim 1, wherein the electrode of each electrode assembly is coupled to a respective wire of the one or more wires.

15. The WCD system of claim 1, wherein the skin-facing surface comprises a silver portion.

16. The WCD system of claim 15, wherein the silver portion is formed with a plurality of openings that are configured to permit airflow.

17. The WCD system of claim 1, wherein the electrode is a two-layer electrode with a first layer interfaced to a skin of the patient and a second layer positioned adjacent to the first layer.

18. The WCD system of claim 17, wherein the impedance and/or thickness of the first layer is different from the impedance and/or thickness of the second layer.

19. The WCD system of claim 1, wherein the plurality of layers include a high-impedance layer having a value of impedance in a range between 1 k$\Omega$ and 100 k$\Omega$.

20. The WCD system of claim 1, wherein the skin-facing surface of the electrode is substantially circular in shape, and wherein the skin-facing surface has a diameter in a range from 0.75 inches to 1.25 inches.

* * * * *